United States Patent [19]
Nelleman et al.

[11] Patent Number: 5,760,401
[45] Date of Patent: Jun. 2, 1998

[54] RESOLUTION ENHANCEMENT APPARATUS AND METHOD FOR DUAL HEAD GAMMA CAMERA SYSTEM CAPABLE OF COINCIDENCE IMAGING

[75] Inventors: Peter Nelleman; Hugo Bertelsen, both of Pleasanton; Horace Hines, San Jose, all of Calif.

[73] Assignee: ADAC Laboratories, Milpitas, Calif.

[21] Appl. No.: 846,525

[22] Filed: Apr. 29, 1997

Related U.S. Application Data

[63] Continuation of Ser. No. 543,116, Oct. 12, 1995, abandoned.

[51] Int. Cl.$^6$ ............................. G01T 1/164; G01T 1/172
[52] U.S. Cl. .................. 250/363.03; 250/363.04; 250/369
[58] Field of Search ................ 250/363.03, 363.04, 250/363.07, 369

[56] References Cited

U.S. PATENT DOCUMENTS

| | | |
|---|---|---|
| 4,675,526 | 6/1987 | Rogers et al. ............ 250/363.02 |
| 5,122,667 | 6/1992 | Thompson . | 
| 5,345,082 | 9/1994 | Engdahl et al. . |
| 5,349,191 | 9/1994 | Roges ................ 250/363.03 X |
| 5,449,897 | 9/1995 | Bertelsen et al. . |
| 5,585,637 | 12/1996 | Bertelsen et al. ........ 250/363.04 X |
| 5,606,166 | 2/1997 | Tararine . |

*Primary Examiner*—Edward J. Glick
*Attorney, Agent, or Firm*—Blakely, Sokoloff, Taylor & Zafman LLP

[57] ABSTRACT

The present invention provides an apparatus and method for enhancing the resolution of a Positron Emission Tomography (PET) image in a Nuclear Camera System that is configurable to performs both PET and SPECT imaging. The apparatus includes a crystal that interacts with a gamma ray to create a scintillation event within the surface of the crystal. The gamma rays that impinge the crystal have an incident angle that is limited by a field of view of the crystal. Positioned behind the crystal is a detector that responds to the light photons released by the scintillation event and registers a coordinate value of the scintillation event. Coupled to the detector is a resolution enhancer that generates an in-crystal plane displacement correction value for the coordinate value registered by the detector. The in-crystal plane displacement correction value is then combined with the coordinate value to compute the actual entry point of the gamma ray into the crystal.

25 Claims, 6 Drawing Sheets

RESOLUTION ENHANCEMENT APPARATUS AND METHOD FOR DUAL HEAD GAMMA CAMERA SYSTEM CAPABLE OF COINCIDENCE IMAGING

This is a continuation of application Ser. No. 08/543,116, filed Oct. 12, 1995, now abandoned.

BACKGROUND OF THE INVENTION

(1) Field of the Invention

The present invention relates to the field of nuclear medicine systems. Specifically, the present invention relates to signal processing systems for scintillation detectors.

(2) Prior Art

Tomographic imaging is one approach to reconstructing an image in nuclear medicine systems. A tomographic image is a two-dimensional representation of structures lying within a selected plane or depth in a three-dimensional object. A computed tomography technique uses individual planes, or "slices," that are physically distinct and nonoverlapping. Generally, the tomographic planes are oriented perpendicular to the long axis of the body; however, other orientations of the planes can also be obtained. By using individual planes, and collecting and processing data only from the tissue section of interest, an accurate representation of the actual activity distribution is obtained.

In contrast to x-ray computed tomography, which uses transmitted radiation, nuclear medicine uses emitted radiation; hence, nuclear medicine techniques generally are referred to as emission computed tomography (ECT). There are two specific types of ECT, single-photon emission computed tomography (SPECT), which uses ordinary gamma-ray emitters, and positron emission tomography (PET), which uses positron emitters.

Gamma cameras performing Single Photon Emission Computed Tomography (SPECT) have been utilized in nuclear medicine for some time. Anger proposed and developed such a system in the 1950s which has been modified and improved extensively with the introduction of high speed digital computer systems for image acquisition as well as image reproduction. In SPECT imaging, gamma ray images are projected by a collimator onto a crystal, creating a pattern of scintillations in the crystal that outlines the distribution of radioactivity in front of the collimator. The collimator projects an image of the source distribution onto the detector by allowing only those gamma rays traveling along certain directions to reach the detector. Typically gamma rays or a certain narrow angle of incidence (approximately perpendicular to the crystal surfaces) actually interacts with the crystal to create a light signal to be collected by photomultiplier tubes in the detector. Gamma rays not traveling in the proper direction are absorbed by the collimator before they reach the detector. The use of a collimator is inherently inefficient. Although SPECT imaging is extensively used in nuclear medicine and provides beneficial image quality, the collimator reduces the sensitivity (i.e. number of gamma rays that actually interacts with the crystal) and therefore reduces the overall resolution and quality of the images acquired by SPECT systems.

Cameras performing Positron Emission Tomography (PET) have also been utilized in nuclear medicine with the introduction of relatively high speed detection electronics and computer systems for image acquisition and processing. The fundamental difference between PET and SPECT is the use of annihilation coincidence detection (ACD) in PET imaging. ACD occurs when two 511-keV photons are emitted in opposite directions following the annihilation of a positron and an ordinary electron. Therefore, only those pairs of events that are detected simultaneously or within a narrow time interval, are recorded by two detectors oriented at 180 degrees to each other.

The overall image quality of a PET system exceeds the image quality of a SPECT system primarily because PET imaging does not utilize a collimator. By eliminating the collimator, the sensitivity of the detector in PET systems is improved. Thus, PET systems can be used to perform medical diagnosis that SPECT systems are not capable of performing, such as tumor surveys and brain scans.

SPECT and PET imaging are generally used for different types of medical diagnosis. In the prior art, different camera systems have been implemented and supplied for PET and SPECT imaging such that a facility desiring to perform SPECT and PET imaging is required to acquire two separate camera systems at a relatively greater expense. Therefore, it would be advantageous to provide a nuclear camera system having the capability to perform both SPECT and PET imaging techniques within a single configurable system.

In order to combine both SPECT and PET imaging techniques into a single nuclear camera system, the system must be capable of performing single photon detection, used in SPECT imaging, and annihilation coincidence detection (ACD) used in PET imaging. Commercially available nuclear camera systems, such as the Vertex system, manufactured by ADAC Laboratories of Milpitas, Calif., have this capability of performing both SPECT and PET imaging techniques in one system.

By incorporating SPECT imaging and PET imaging into one system, the same scintillation crystal is used for both the SPECT and PET imaging. However, SPECT imaging and PET imaging implemented in different nuclear camera systems use different types of crystals. Typically, SPECT imaging uses a crystal made of crystalline sodium iodide doped with thallium NaI(Tl) to provide sufficient stopping power for a single photon in SPECT imaging. On the other hand, stand-alone, prior art PET systems use detectors with greater stopping power than detectors used in SPECT imaging. The preferred detector material for PET imaging is bismuth germanate oxide (BGO) because of its higher density and atomic number which provides sufficient stopping power for the 511 keV annihilation gamma rays generated by the positron emission. Furthermore, the crystal elements are arranged in a grid-like array. When an incoming gamma ray intersects the BGO crystal, the detector is able to detect the actual point of intersection of the gamma ray from the grid-like crystal formation. Although NaI(Tl) and BGO are described as being the preferred crystals for SPECT and PET imaging, respectively, other crystals well known in the art may be substituted.

However, when NaI(Tl) crystals are substituted for BGO crystals in PET imaging, such as in a combined SPECT and PET system, and the collimator is removed, the resolution and quality of the image reconstructed by PET imaging is degraded. Without a collimator, the incoming gamma rays intercept the NaI(Tl) crystal at a wide variety of angles, rather than the narrow range of angles (approximately perpendicular to the crystal surface) used in the SPECT systems. When a gamma ray interacts with the NaI(Tl) crystal during PET imaging, the conversion of gamma rays, to light photons takes place some distance within the crystal plane. Therefore, if the gamma ray is impinging the surface of the crystal at a slant angle, the registration by the detector will be displaced by some distance. In other words, the larger the incident angle and the in-crystal plane displacement of the in-coming gamma ray, the larger the resolution degradation of a point source. Thus, it is desirable to provide a resolution enhancement apparatus and method to correct this type of distortion which reduces the overall quality of the image reconstructed in PET imaging.

SUMMARY OF THE INVENTION

An object of the present invention to provide a Nuclear Camera System that is capable of both PET and SPECT imaging with improved resolution during PET imaging.

Another object of the present invention is to enhance the resolution of an object by correcting the distortion caused by in-crystal plane displacement that occurs when gamma rays interact with a crystal, such as NaI(Tl).

Furthermore, an object of the present invention is to compute in-crystal plane displacement values. Once the in-crystal plane displacement values are determined, the coordinate values representing the registered location can be modified to represent the actual point of entry of the gamma rays within the crystal.

An apparatus for enhancing the resolution of Positron Emission Tomography (PET) images in a Nuclear Camera System that is configurable to perform both PET and SPECT imaging is described. The apparatus includes a crystal that creates a scintillation event within the surface of the crystal when the crystal interacts with a gamma ray. The gamma rays that impinge the crystal have an incident angle that is limited by a field of view of the crystal. Positioned behind the crystal is a detector that responds to the light photons released by the scintillation event and registers a coordinate value of the scintillation event. Coupled to the detector is a resolution enhancer circuit that generates an in-crystal plane displacement correction value for the coordinate value registered by the detector. The in-crystal plane displacement correction value is then combined with the coordinate value to compute the actual entry point of the gamma ray into the crystal.

Another apparatus of the present invention improves the resolution in PET imaging (i.e., coincidence imaging) is described. The apparatus includes a pair of detectors for simultaneously detecting a pair of gamma rays generated from a source point and emitted 180 degrees apart. When each gamma ray interacts with a crystal positioned in front of the detector, a scintillation event occurs. The first detector generates a first address signal that represents the localization of an event in a first crystal and the second detector generates a second address signal that represents the localization of an event in a second crystal. A computer system is coupled to the pair of detectors for receiving the first and second address signals and generating a first and a second correction value to correct the in-crystal plane displacement value of the impinging gamma rays. The computer system then corrects the first and second address signals and outputs these corrected signals to an image processor to be used for image processing and reconstruction.

A method to enhance the resolution in a Nuclear Camera System capable of PET (coincidence) imaging is also described. A crystal receives a gamma ray having an incident angle within a range of angles limited by a field of view of the crystal. Detectors, positioned on the backside of the crystal, detects the scintillation event that occurs when the crystal interacts with the impinging gamma ray and registers the coordinate value of the scintillation event. After the coordinate values are registered, a processor generates a correction value to correct the in-crystal plane displacement of the registered coordinate value and then combining the correction value with the registered coordinate value to determine the actual point of entry of the gamma ray into the crystal.

DETAILED DESCRIPTION OF THE INVENTION

In the following detailed description of the present invention numerous specific details are set forth in order to provide a thorough understanding of the present invention. However, it will be obvious to one skilled in the art that the present invention may be practiced without these specific details. In other instances well known methods, procedures, components, and circuits have not been described in detail as not to unnecessarily obscure aspects of the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. Unless specifically stated otherwise as apparent from the following discussions, it is appreciated that throughout the present invention, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Figure 1:
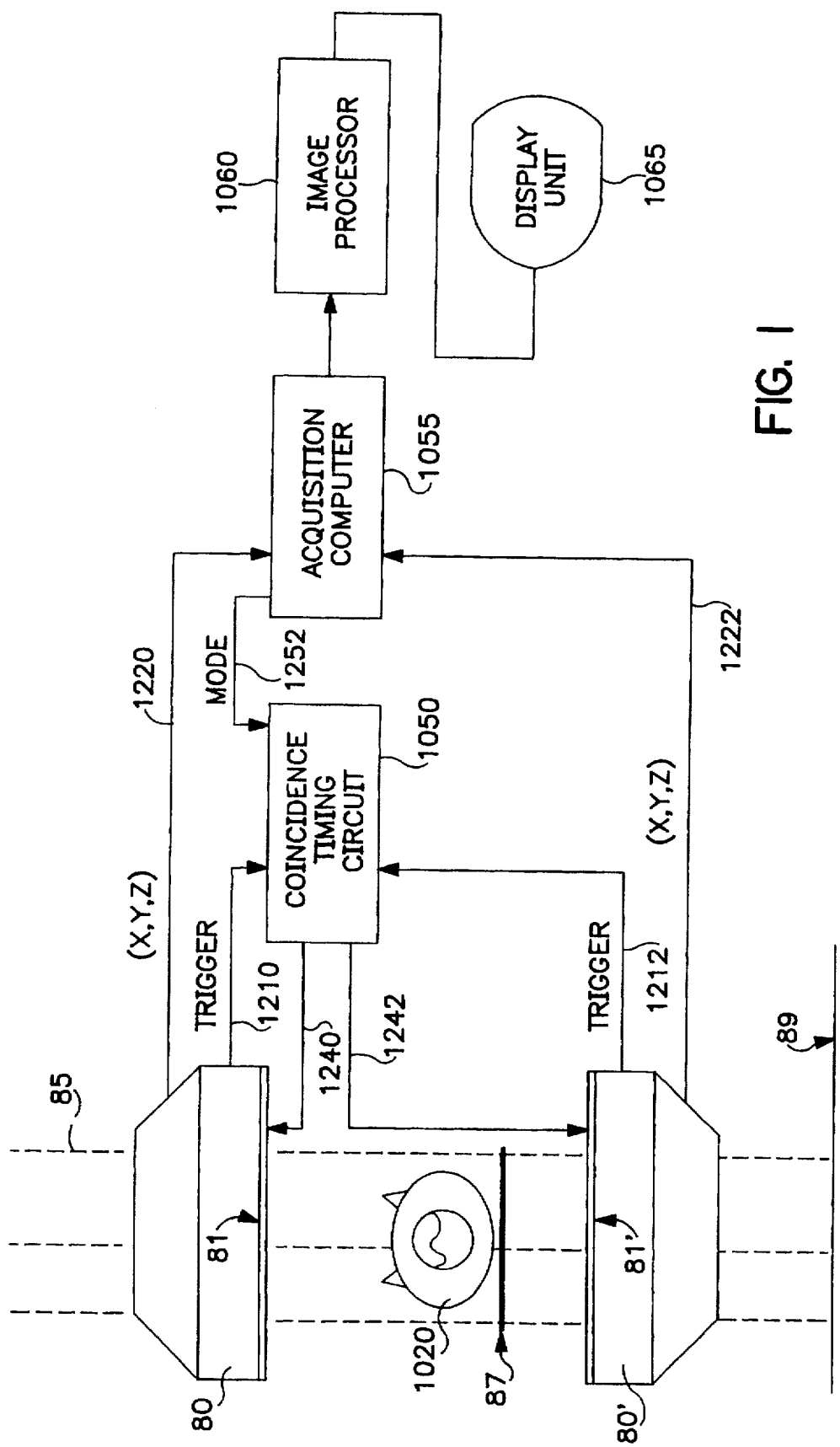
FIG. 1 illustrates a high level block diagram of a Dual Head Gamma Camera System of the present invention that is capable of performing both SPECT and PET imaging.

The present invention provides a nuclear camera system capable of operating in both PET and SPECT modes with improved imaging of a radionuclide distribution during PET mode. Although the present invention is described in conjunction with a configurable (SPECT or PET) camera system, this invention is not limited to a configurable camera system and may be used in a stand-alone PET imaging system. It is appreciated that the present invention can advantageously operate within a camera system having more than two detector heads. With reference to FIG. 1, a high level diagram of a dual head nuclear camera system of the present invention is shown. Although an embodiment of the present invention is described with respect to a two detector camera system, it is appreciated that the teachings of the present invention can be extended to cover systems having more than two detectors (e.g., it can be extended to triple and quadruple camera systems). The detector pair is shown in a 180 degree configuration and can rotate with respect to each other such that they are at a 90 degree configuration. Generally, the system of the present invention includes a pair of gamma camera detectors 80 and 80' ("dual head") composed of a plurality of photomultiplier tubes, PMTs, arranged in a two dimensional matrix and coupled to crystals 80 and 80' to receive light (e.g., visible photons). The PMT array creates a photodetector. It is appreciated that each detector, either 80 or 80', is similarly constructed and that discussions with respect to one detector are applicable to both.

The crystal layers 81 and 81' can be composed of sodium iodine (NaI) that is doped with thallium (Tl), and is typically located between a collimator (not shown) and the PMT array during SPECT imaging. However, during PET imaging a collimator is not used. Typically, a collimator includes a number of holes with lead septas arranged in a honeycomb convention. The collimator projects an image of the source distribution onto detectors 80 and 80' by allowing only those gamma rays traveling along certain directions to reach the detector. In an embodiment of the present invention, only gamma rays impinging crystals 81 and 81' at approximately 90 degrees is detected by detectors 80 and 80'. Gamma rays not traveling at approximately 90 degrees are absorbed by the collimator before they reach detectors 80 and 80'.

Gamma rays that strike the NaI(Tl) crystal 81 cause well known scintillation events that release a number of visible light photons that are detected by the PMTs. In the present invention the PMTs are arranged in a hexagonal pattern. However, the number of PMTs, their sizes and their configurations can be varied within the scope of the present invention. During SPECT mode, 19 PMTs are used to detect a scintillation event. The PMT closest to the event, the first ring of 6 PMT's adjacent to this PMT, and the next ring of 12 PMT's comprise the 19 PMT tubes. During PET mode 7 PMTs are use to detect an event. The 7 PMT tubes include the tube nearest to the event and its 6 nearest neighbors.

The PMT tubes used to detect an event provide analog signals representing the amount of light energy detected. Therefore, if a scintillation event occurs at a point A in a crystal, the PMTs closest to the event will receive the greatest amount of light and thus will provide output signals of the greatest amplitude. These analog signals reported by the PMTs are used for event localization. In the present invention, these analog signals are digitized by circuitry within detectors 80 and 81'. The gamma camera detectors 80 and 80' utilized within the scope of the present invention are of the type used in digital gamma cameras and can be of a number of well known and commercially available designs, and therefore some details of such a gamma detector will not be discussed in depth herein. A digital gamma camera is described in U.S. Pat. No. 5,449,897, issued Sep. 12, 1995, to ADAC Laboratories.

The detectors 80 and 80' are mounted on a gantry 85 which can rotate the detectors 80 and 80' in various orbits (ECT projections) around an object (patient) 1020 resting on table 87 (e.g., for ECT scanning operations). In either configuration (180 or 90 degrees), the detector pair can rotate about a center of rotation through a number of projection angles, as is known in gamma camera technology. The gantry 85 and table 87 rest on base 89. The detector pair 80 and 80' can also be directed transversely across the table 87 (e.g., for total body scanning operations) or placed over the patient 1020 for static imaging.

Upon an event detection in either detector 80 or 80', signals 1210 and 1212, respectively, carry initial event detection trigger pulses to a programmable coincidence timing circuit 1050 (CTC). The CTC unit 1050 then generates valid event trigger signals over lines 1240 and 1242, respectively, back to the detectors for the 80 and 80' depending on the mode of operation (either SPECT or PET). A signal carried over line 1252 indicates to the CTC unit 1050 the proper mode of operation (SPECT or PET). The valid event trigger signals 1240 and 1242 are used by the detectors to start (or reset) their accumulators (integrators) which accumulate (integrate) the energy of the detected scintillation and are therefore called "valid event" trigger signals. In the PET mode, integration is not started until a coincidence is detected between detector 80 and 80'. In SPECT mode, an integration is started for each detector upon a trigger event, regardless of coincidence. After integration and centroiding, the detectors 80 and 80' output an X, Y, and Z value over lines 1220 and 1222, respectively. These signals indicate the coordinate values X and Y representing the "localization" of the detected event and its measured energy value, Z.

Within embodiments that utilize more than two detector heads, event detection information from each detector head is forwarded to the CTC unit 1050 that then detects coincidence between any two detectors feeding the CTC event detection information (when in PET imaging mode). In SPECT mode, each detector reports event information in non-coincidence in a similar fashion as the dual detector system.

Although the location of such hardware is not material to the present invention, hardware is included within each detector for digitizing the PMT analog signals and outputting X, Y, and Z values. To this extent, each detector 80 and 80' contains pre-amplification and digitization hardware and a digital event processor. This hardware can be located within or outside the scintillation detectors 80 and 80'.

The values transmitted over bus 1220 and bus 1222 provides inputs to an acquisition computer 1055 which is a general purpose digital computer system. The acquisition computer 1055 stores and modifies the values for each detected event for each projection angle and then routes this information to an image processor 1060 which has a standard user interface. The user interface provides a user input device for indicating which mode of operation (e.g. SPECT or PET) is requested. The user input device can also be located in computer 1055.

In the image processor 1060, the event localization data associated with various ECT projection angles are stored in a memory device. This data is used to generate image information and count density information and is collected in the form of a matrices for the different ECT projection angles. Image matrices are generally collected at different ECT angles and then a reconstruction is done, using tomographic reconstruction to generate a three-dimensional image ("reconstruction") of an organ. The image processor 1060 is also coupled to a display unit 1065 (which can include a hard copy device) for visualizing images captured by the camera system.

The present invention provides an apparatus and a method for enhancing the resolution of a radionuclide distribution during PET imaging, also known as coincidence imaging. The present invention corrects the in-crystal plane displacement of a gamma ray impinging the crystal at a slant angle. Typically, the in-crystal plane displacement in SPECT imaging is relatively small because the collimator only allows gamma rays having a narrow range of incident angles to impinge the NaI(Tl) crystal. Furthermore, stand-alone PET imaging systems that use a discrete crystal such as bismuth germanate oxide (BGO) do not have in-crystal plane displacement of the incident gamma ray due to the nature of the discrete crystal. However, when PET imaging is implemented in a configurable SPECT/PET nuclear camera system, the BGO crystal may be replaced with a NaI(Tl) crystal such that in-crystal plane displacement causes resolution degradation. Therefore, the procedure to correct the in-plane crystal displacement of an impinging gamma ray is most applicable when a crystal, such as NaI(Tl), is used in PET imaging.

Figure 2:
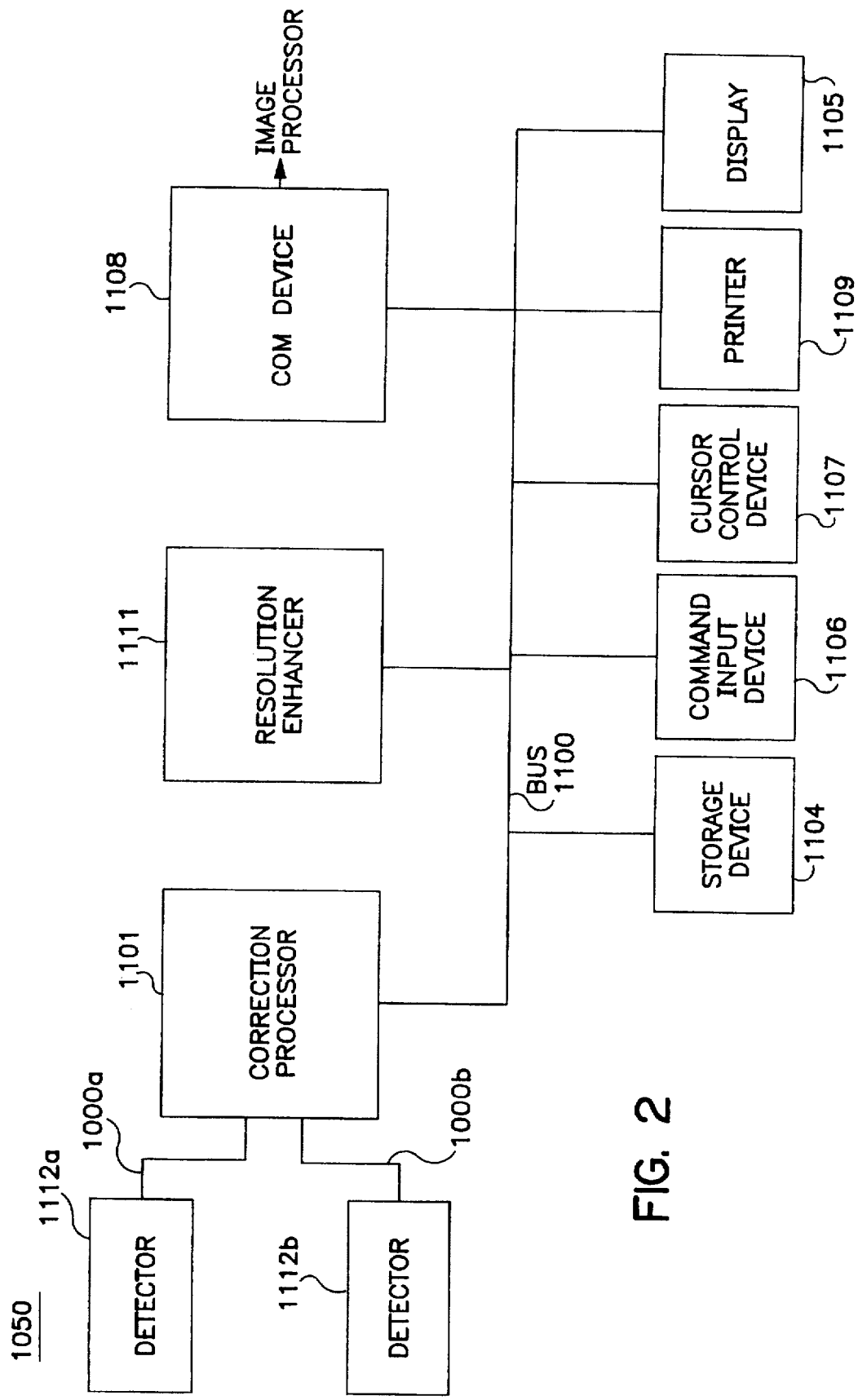
FIG. 2 illustrates a block diagram of the Acquisition Computer in the Dual Head Gamma Camera System.

FIG. 2 is a block diagram of Acquisition Computer 1050 coupled to detectors 1112a and 1112b. Acquisition Computer 1050 is responsible for correcting the distortion caused by the gamma rays intercepting the crystals at a slant angle. Acquisition Computer 1050 comprises an address/data bus 1100 for communicating information within Acquisition Computer 1050; a correction processor 1101 coupled with the bus 1100 for energy, linearity and correction of gamma rays impinging the crystal at approximately 90 degrees; a resolution enhancer 1111 coupled to bus 1100 for correcting the in-crystal plane displacement of gamma rays impinging the crystal at a slant angle; a data storage device 1104 such as a magnetic or optical disk drive coupled with the bus 1100 for storing image information and instructions from a processor; a display device 1105 (which can also be external such as device 1065 of FIG. 1) coupled to the bus 1100 for displaying information to the computer user; an alphanumeric input device 1106 including alphanumeric and function keys coupled to the bus 1100 for communicating information and command selections to a processor; a cursor control device 1107 coupled to the bus for communicating user input information and command selections to a processor; and a high speed communications link 1108 coupled to the bus 1100 for communicating with an image processor. A hard copy device 1109 (e.g., printer) may also be coupled to bus 1100.

The display device 1105 of FIG. 2 (or the display unit 1065 of FIG. 1) utilized with the Acquisition Computer 1050 of the present invention can be a liquid crystal device, cathode ray tube, or other display device suitable for creating graphic images and alphanumeric characters recognizable to the user. The cursor control device 1107 allows the computer user to dynamically signal the two dimensional movement of a visible symbol (pointer) on a display screen of the display device 1105. Many implementations of the cursor control device are known in the art including a trackball, finger pad, mouse, joystick or special keys on the alphanumeric input device 1105 capable of signaling movement of a given direction or manner of displacement. The keyboard 1106, the cursor control device 1107, the display 1105 and hard copy device 1109 comprise the user interface associated with the image processor 1060.

Figure 3:
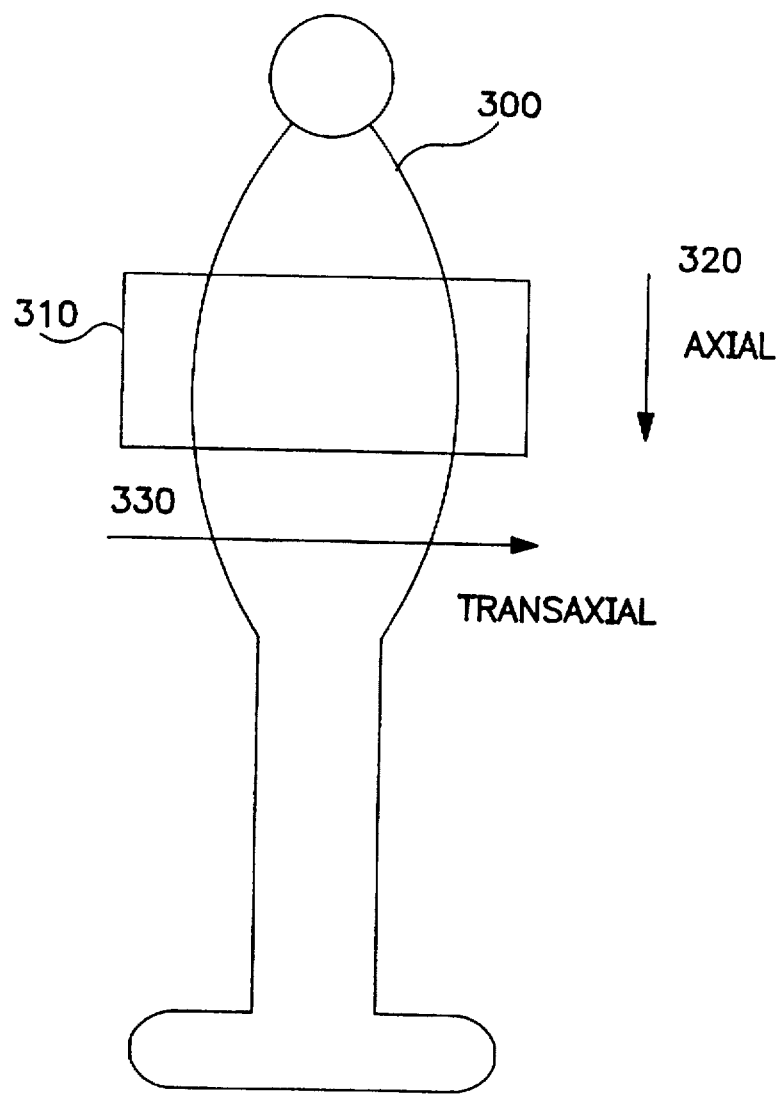
FIG. 3 is an illustration of the axial and transaxial field of views of the crystal surface in the present invention.

When operating in PET mode, the coordinate values X and Y, and energy information Z are generated from each detector 1112a and 1112b within a coincidence window. The X and Y coordinates detected by scintillation detectors 1112a and 1112b correspond to a point within the crystal where the scintillation event occurs. The X coordinate corresponds to the location of the scintillation event along the transaxial field of view of the crystal and the Y coordinate corresponds to the location of the scintillation event along the axial field of view of the crystal. FIG. 3 provides an illustration of the transaxial and axial field of view of detectors 1112a and 1112b with respect to patient 300 who has been injected with a radionuclide and is emitting gamma rays from one or more of his organs. Rectangle 310 represents the field of view of one of the detectors 1112a or 1112b. According to FIG. 3, the axial field of view of a crystal is shown by arrow 320 and is oriented across the patient from top to bottom, and the transaxial view is shown by arrow 330 and is oriented across the patent from left to right. Although detectors 1112a and 1112b have a rectangular field of view in FIG. 3, the present invention is not limited to detectors having a rectangular surface area.

The coordinate values X and Y of the two detected points are registered by detectors 1112a and 1112b and are outputted over lines 1000a and 1000b, respectively, to the Acquisition Computer 1055. Correction Processor 1101, Resolution Enhancer 1111, and Com Device 1108 are included within the Acquisition Computer 1055. From this pair of coordinate values X and Y, the axial and transaxial angles of incidence of the in-coming gamma ray are computed by Acquisition Computer 1055. The position of the annihilation of a positron and an ordinary electron (or scintillation event) lies along the line connecting the two points detected. In the event there is in-crystal plane displacement, the X and Y coordinates registered by scintillation detectors 1112a and 1112b do not accurately represent the actual point of interception of the impinging gamma rays. Furthermore, if the source point (i.e. the location within an organ that is emitting radiation) is not along the centerline between detectors 1112a and 1112b oriented 180 degrees apart, then the in-crystal plane displacement causes distortion or blurring of the source point when the image is reconstructed.

In an embodiment of the present invention, coordinate values X and Y registered by detectors 1112a and 1112b are outputted via lines 1000a and 1000b to Correction Processor 1101. Correction Processor 1101 modifies coordinate values X and Y to improve the intrinsic resolution. Intrinsic resolution, which is the statistical variations in the distribution of light photons among the photomultiplier tubes (PMT), creates a certain amount of distortion to the gamma ray impinging the crystal. Therefore, Correction Processor 1101 modifies coordinate values X and Y and outputs new coordinate values X' and Y' on bus 1100. Coordinate values X' and Y' are then modified by Resolution Enhancer 1111 to correct for the in-crystal plane displacement of the incident gamma rays. As mentioned above, the in-crystal plane displacement occurs when the incident angle of the gamma rays intersect a crystal, such as NaI(Tl), at a slant. Thus, this invention is particularly relevant to PET imaging in a nuclear camera system that performs both PET and SPECT imaging.

Figure 6:
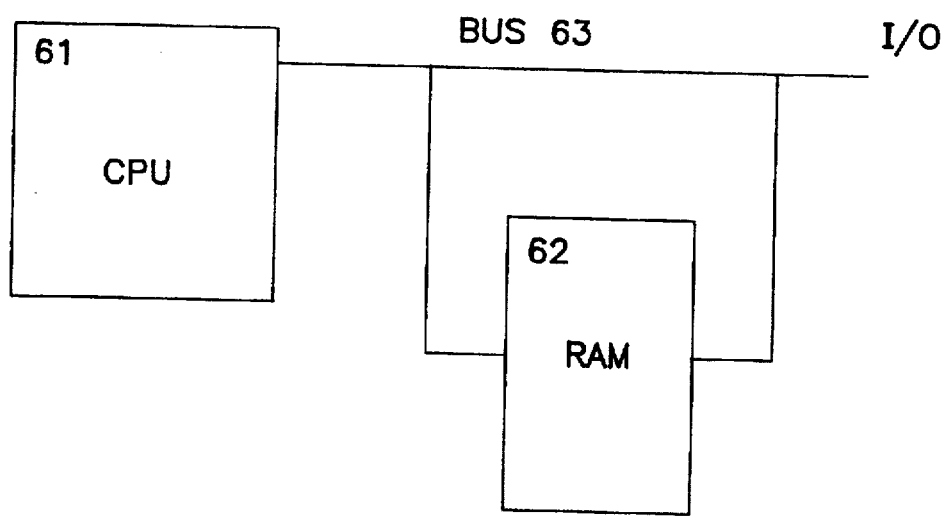
FIG. 6 is a block diagram illustration of the Image Einhancer in the present invention.

Resolution Enhancer 1111 is a processor that computes the in-crystal plane displacement values for PET imaging. According to FIG. 6, Resolution Enhancer may be a computer system 60 comprising of an Central Processing Unit (CPU) 61 and Random Access Memory (RAM) 62. In one embodiment of the present invention, CPU 61 is a Pentium™ processor operating at 100 MHz. CPU 61 is coupled with bus 63 for executing instructions and processing information and RAM 62 is coupled with the bus 63 for storing information and instructions for the CPU 61.

RAM 62 stores the coordinate values X' and Y' for each scintillation event registered by each of the detectors 1112a and 1112b. Coordinate values X' and Y' may be the same values as coordinate values X and Y recorded by one of the detectors 1112a or 1112b, or they may be a modified version of coordinate values X and Y. CPU 61 generates the in-crystal plane displacement values ΔX and ΔY for the X' and Y' coordinate values. A pair of in-crystal plane displacement values ΔX and ΔY is generated for each positron-electron interaction involved in coincidence imaging. Thus, ΔX is the displacement value of an incident gamma ray with respect to the transaxial field of view of the crystal and ΔY is the displacement value of an incident gamma ray with respect to the axial field of view of the crystal. Once the displacement values ΔX and ΔY are computed, these values are combined with coordinate values X' and Y'. In one embodiment of the present invention, the displacement values ΔX and ΔY are added from coordinate values X' and Y' such that the corrected coordinate values (X'+ΔX) and (Y'+ΔY) are outputted to the image processor.

This type of correction becomes extremely important as the incident angle of the gamma rays increases since the in-crystal plane displacement increases as the incident angle increases. In an embodiment of the present invention, the transaxial field of view is larger than the axial field of view, therefore, the most noticeable in-crystal plane displacement occurs along the transaxial field of view. The present invention applies to both views.

Figure 4:
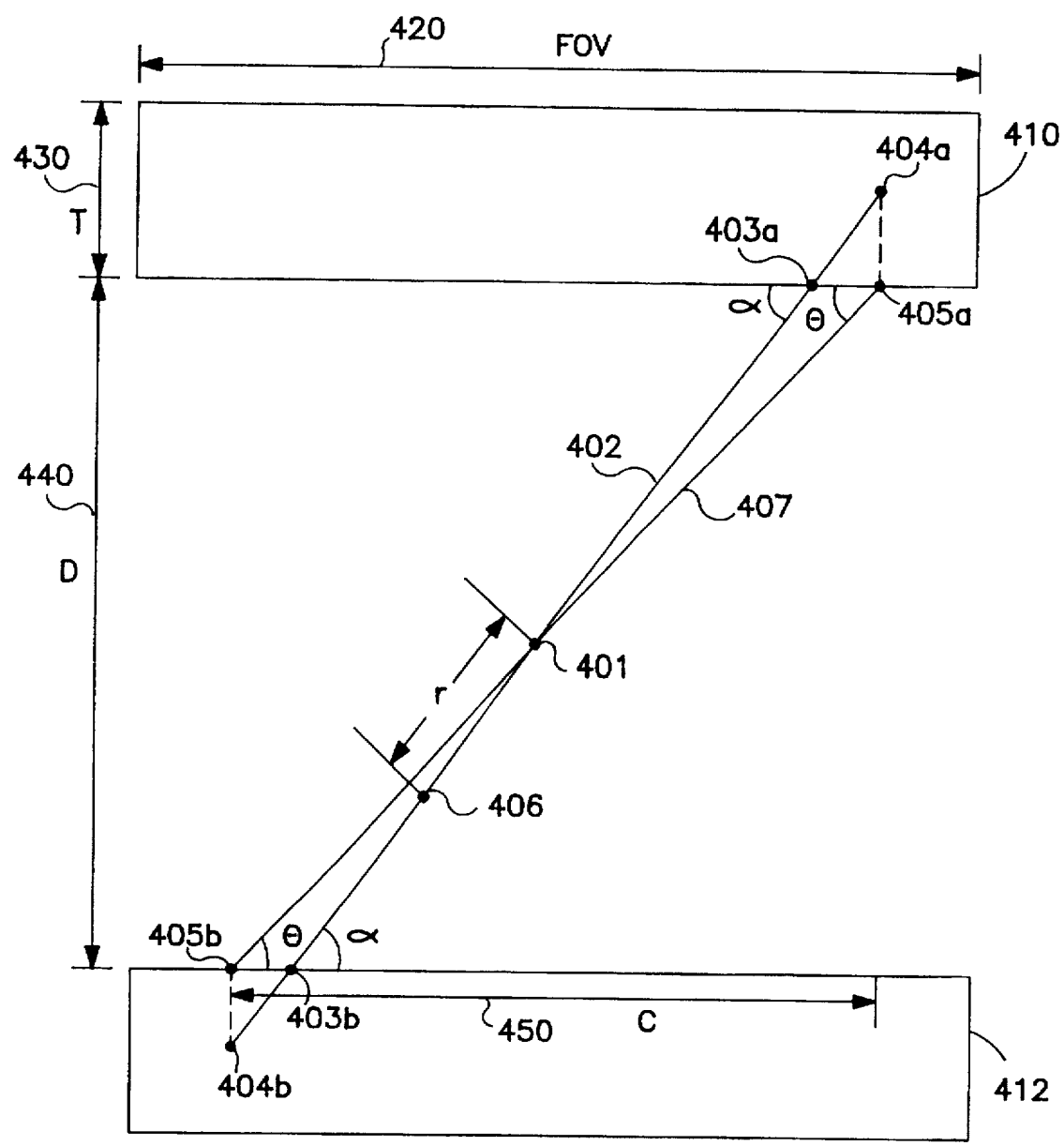
FIG. 4 is a cross sectional view of a pair of crystals illustrating the interaction of a gamma ray with each of the crystals.

FIG. 4 provides a cross sectional view of the crystal 410 and 412 oriented 180 degrees apart and is used to graphically illustrate the in-crystal plane displacement with respect to a pair of gamma rays generated from the annihilation of a positron with an electron at a point 401. Line 420 represents either the axial or transaxial field of view of crystals 410 and 412. Line 430 represents the depth or thickness, T, of crystals 410 and 412 and line 440 represents the distance, D, between crystals 410 and 412. The positron-electron interaction point, also known as the source point, is located along the center-line at a point 401. The two gamma rays emitted from the positron-electron interaction are generated in roughly opposite directions along the line of response 402. One of the gamma rays emitted intercepts crystal 410 at a point 403a and creates a scintillation event at a point 404a. The second gamma ray emitted intercepts crystal 412 at a point 403b and creates a scintillation event at a point 404b. Points 403a, 403b, 404a and 404b are all located along the line of response 402 of the positron-electron interaction that occurs at point 401. α is the incident angle of the pair of gamma ray intercepting crystals 410 and 412 at points 403a, 403b, respectively.

When a positron-electron interaction occurs at a point 401, the actual point of entry into crystal 410 is at 403a, although a detector positioned behind crystal 410 registers the entry point as occurring at point 404a with respect to the field of view 420. Therefore, there is a displacement (Δ1) along field of view 420 between the actual point of entry 403a into crystal 410 and the point registered 404a by the detector of the incident gamma ray. Furthermore, the actual point of entry into crystal 412 is at 403b but the detector registers the entry point as occurring at point 404b along to the field of view 420. Thus, Δ2 is the displacement between the actual point of entry 403b into crystal 412 and the point registered 404b by the detector. In other words, Δ1 is the distance between point 403a and 405a and Δ2 is the displacement between point 403b and 405b. Δ1 and Δ2 are also known as the in-crystal displacement values since the registered locations (404a and 404b) represent the actual point of entry (403a and 403b) displaced by a certain distance Δ1 and Δ2.

Computing the in-crystal plane displacement and correcting the registered coordinate value X and Y to take into account for the displacement, enhances the resolution of the image of the radionuclide distribution. Source point 401 is located along the center-line such that the in-crystal plane displacement Δ1 and Δ2 are approximately equal and the detectors register the point of interception of the gamma ray with the crystal at points 405a and 405b. If a line is drawn from a point 405a to a point 405b, that line will pass through the source point 401 such that the location of the source point can be determined from the registered values of the source point along the field of view 420. However, this is only true when the source point 401 is not located mid-way between crystal 410 and 412, (i.e. the center-line). In the event a source point 406 is located some distance r along the line of response 402 and away from the center line, then the detectors will also sense that the gamma rays impinge the crystal along field of view 420 at points 405a and 405b. When a line is drawn from 405a to 405b, this line 407 does intersect the source point 406 and therefore, the location of the source point 406 can not be accurately determined and the resolution of the source point 406 is degraded. As the resolution of the source point is degraded, the reconstructed image of the source point gets blurred.

Figure 5:
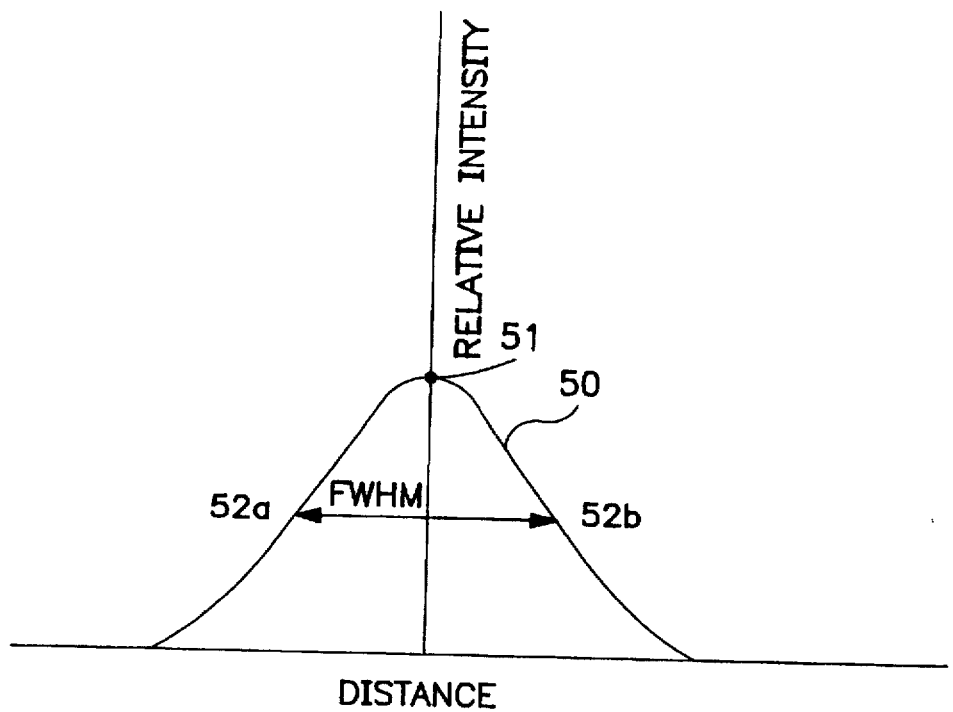
FIG. 5 illustrates the projected radiation profile (i.e. resolution) of a point source.

By generating in-crystal plane displacement values for each scintillation event detected in coincidence, the resolution of each source point can be improved, thereby improving the overall quality of the image reconstructed. FIG. 5 graphically illustrates the resolution of a source point with the horizontal axis representing the relative intensity of the source point and the vertical axis representing the distance along the crystal surface of the radiation profile. The frequency distribution curve 50 represents the projected radiation profile of a source point having a mean value at point 51. The full width at half maximum, FWHM, is measured between the two points 52a and 52b and indicates where the intensity is one-half of the mean value. The resolution of the source point is defined as the FWHM of the radiation profile from a source point of radiation projected onto a detector. Therefore, as FWHM is increased, the resolution is degraded, causing more distortion of a point source. By correcting for in-crystal plane displacement, the FWHM is reduced and the resolution is enhanced.

In an embodiment of the present invention, CPU 61 generates a displacement value Δ during PET imaging in the following manner. The displacement value Δ may represent the in-crystal plane displacement along the transaxial or axial field of view of either detector 410 or 412. For purposes of this illustration, the displacement value Δ is measured along the transaxial field of view of crystal 412 and is therefore referred to as displacement value ΔX.

Referring back to FIG. 4, ΔX is computed with respect to source point 406. The annihilation of a positron and an ordinary electron occurs at source point 406 which emits two 511-keV photons in opposite directions along line 402. Only those pairs of events that are detected simultaneously, or within a narrow time interval, are registered by detectors 410 and 412, which are oriented at 180 degrees to each other. The actual point of entry of a gamma ray into crystal 412 is at 403b, however, the detector registers point 404b as the actual point of entry. Furthermore, the actual point of entry of a gamma ray into crystal 410 is at 403a, however, the detector registers point 404a as the actual point of entry. Therefore, the source point 406, appears to the detectors to be located along line of response 407 which is projected from 405b to 405a. The distance D between crystal 410 and 412 is shown by line 440 and the distance C between the point 405a and 405b is shown by line 450. Based on the line of response 407, the distance D and the distance C, the angle θ is computed with respect to the crystal plane 410 and 412. The incident angle θ can be computed from the following equation θ(C)=ATAN(D/C).

Although, the incident angle of the gamma rays emitted along line of response 402 is equal to α, the incident angle θ is a close enough estimate of incident angle α to be used in the computations of the displacement value ΔX.

Figure 7:
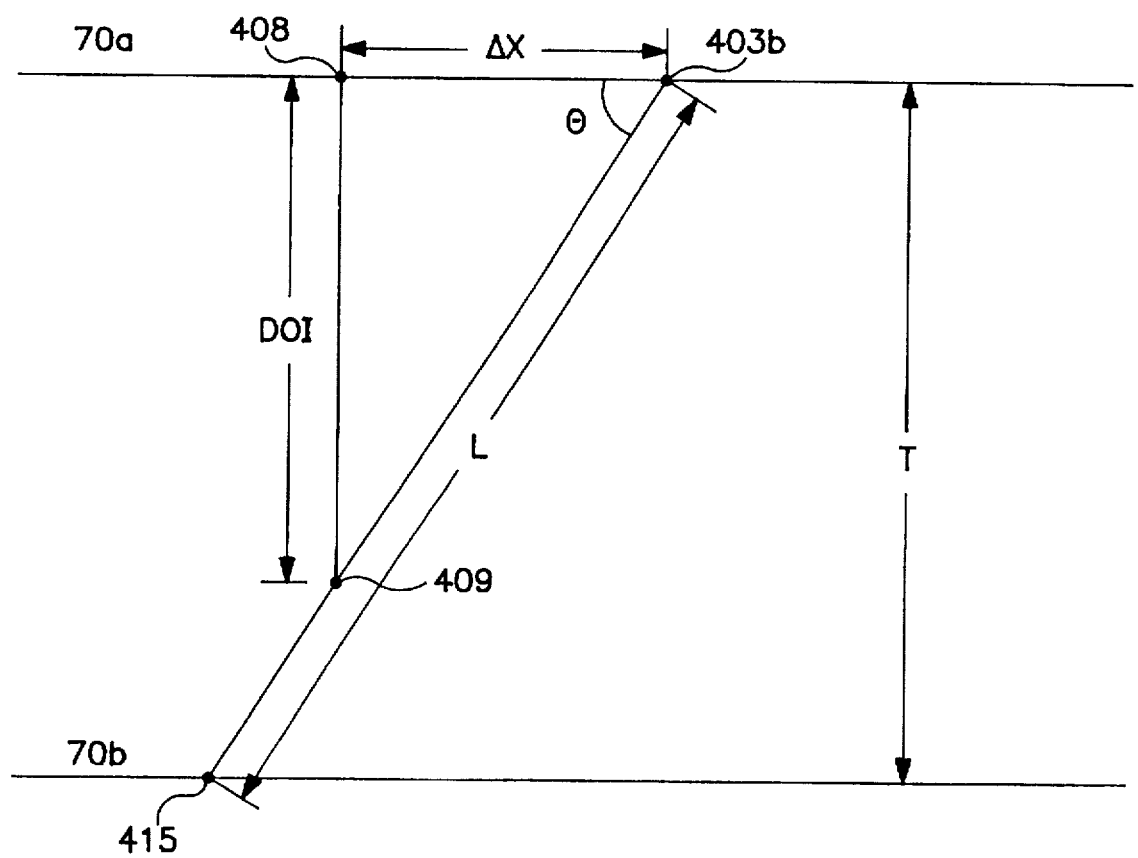
FIG. 7 illustrates the in-crystal plane displacement value when a gamma ray interacts with a crystal.

Once the angle θ is computed, the parameters L and DOI in FIG. 7 can also be computed. FIG. 7 represents a cross section of crystal 412 having a front surface 70a intercepting gamma rays and back surface 70b positioned in front of the PMTs. L represents the maximum distance that the gamma ray may travel along line of response 402 into the crystal plane of crystal 412 and is the distance between 403b and 415. L can be calculated by the following equation $$L(\theta) = \sqrt{T^2 + \left(\frac{T}{\text{TAN}(\theta)}\right)^2}$$

where T is the thickness of crystal 412. In one embodiment of the present invention, T is three eighths of an inch thick. DOI is the average depth of interaction and represents the location 409 within the crystal that the gamma ray has the highest probability of an interaction (or creating a scintillation event) with crystal 412. A line is projected from a point 409 perpendicular to crystal plane 70a such that DOI is the distance between a point 408 and a point 409. Although the scintillation event within the crystal 412 has the highest probability of occurring at 409, the scintillation event may not occur exactly at that point 409. DOI is related to the attenuation A(x) of the 511 keV gamma rays traveling through the NaI(Tl) crystal, the density ρ of the NaI(Tl) crystal, and the mass attenuation coefficient $\mu_m$ at 511 keV of the NaI(Tl) crystal. In one embodiment of the present invention $\mu_m$=0.0921 cm²/gm, ρ=3.67$^{gm}$/cm³ and $A(x)=e^{-\mu_m \rho x}$. The DOI can be calculated from the following equation $$DOI(\theta) = \frac{\int_0^{L(\theta)} xA(x)dx}{\int_0^{L(\theta)} A(x)dx} * \text{SIN}(\theta).$$

Once DOI and L are computed, the in-crystal plane displacement ΔX can be determined from the following equation ΔX=DOI(θ)*COT(θ).

Once the displacement values ΔX and ΔY are computed, these values are combined with coordinate values X' and Y'. In one embodiment of the present invention, the displacement values ΔX and ΔY are subtracted to coordinate values X' and Y' such that the corrected coordinate values (X'-ΔX) and (Y'-ΔY) are outputted to the image processor.

In PET Imaging, the incident angle of the pair of gamma rays emitted will be detected if they interact with the crystal, in coincidence, anywhere within the crystal's axial and transaxial field of views. In other words, in PET imaging the incident angle of the gamma rays is limited by the field of view 420 of crystals 410 and 412. Furthermore, the larger the in-crystal plane displacement, the larger the degradation in the resolution. In SPECT imaging, the incident angles is limited to a very narrow range (approximately 90 degrees) by the collimator such that very little in-crystal displacement occurs. Furthermore, stand-alone PET imaging system that use a discrete crystal, such as bismuth germanate oxide (BGO), do not have in-crystal plane displacement due to the nature of the discrete crystal. Thus, this resolution enhancement apparatus and procedure of the present invention is most beneficial for PET Imaging in a combined SPECT and PET system, that utilizes a crystal, such as sodium iodide doped with thallium NaI(Tl).

What is claimed is:

1. An apparatus for improving resolution of coincidence imaging in a nuclear camera system, comprising:
    a first detector and a second detector configured to detect coincidentally a pair of gamma rays emitted from a source point 180 degrees apart, wherein said first detector provides a first address signal and said second detector provides a second address signal, wherein said first address signal includes a first x value and a first y value and said second address signal includes a second x value and a second y value, wherein said first x value corresponds to a transaxial field of view of said first detector, said second x value corresponds to a transaxial field of view of said second detector, said first y value corresponds to an axial field of view of said first detector, and said second y value corresponds to an axial field of view of said second detector; and
    a computer system coupled to said first detector and said second detector and configured to receive said first address signal and said second address signal, wherein said computer system is further configured to provide a first correction value and a second correction value to correct an in-crystal plane displacement of a scintillation event wherein said first correction value includes an x component and a y component, such that said x component of said first correction value is added to said first x value of said first address signal and said y component of said first correction value is added to said first y value of said first address signal, wherein said second correction value includes an x component and a y component, such that said x component of said second correction value is added to said second x value of said second address signal and said y component of said second correction value is added to said second y value of said second address signal, wherein said computer system is further configured to output a corrected first address signal and a corrected second address signal.

2. The apparatus of claim 1, wherein said x component of said first correction value and said x component of said second correction value are dependent on an energy level of said pair of gamma rays and an incident angle of said pair of gamma rays along said transaxial field of view of said first detector and said second detector, respectively, said y component of said first correction value and said y component of said second correction value are dependent on said energy level of said pair of gamma rays and said incident angle of said pair of gamma rays along said axial field of view of said first detector and said second detector, respectively.

3. The apparatus of claim 1, wherein said first and second detectors comprise thallium-activated sodium iodide crystals NaI(Tl).

4. A method for improving the resolution of an image in a gamma camera system configurable to perform either single-photon emission computed tomography imaging or positron emission tomography imaging, the method comprising the steps of:
    (a) operating at least one of a plurality of detectors of the gamma camera system, the detectors configurable to operate in either a coincidence detection mode or a single-photon detection mode, to receive a first gamma ray having an incident angle, said plurality of detectors including a scintillator;
    (b) detecting a first scintillation event in the scintillator;
    (c) registering a first coordinate value of said first scintillation event;
    (d) generating a first correction value to correct a plane displacement of said first coordinate value; and (e) combining said first correction value with said first coordinate value to determine an entry point of said first gamma ray into said scintillator.

5. The method of claim 4, wherein the registering step (c) includes the steps of:
   (i) registering an x coordinate value along a transaxial field of view of said scintillator; and
   (ii) registering a y coordinate value along an axial field of view of said scintillator.

6. The method of claim 4, wherein the generating step (d) includes the steps of:
   (i) generating an x delta value which is the distance along a transaxial field of view of said scintillator between said entry point of said gamma ray into said scintillator and a conversion point, wherein said conversion point is a point where said gamma ray has the highest probability of interacting to cause a scintillation event inside said scintillator; and
   (ii) generating a y delta value which is the distance along an axial field of view of said scintillator between said entry point of said gamma ray into said scintillator and said conversion point.

7. The method of claim 6, wherein the step (i) of generating, an x delta value includes the steps of:
   (i) measuring said incident angle of said gamma ray along said transaxial field of view of said scintillator;
   (ii) determining a depth of interaction of said gamma ray in said scintillator; and
   (iii) generating said x delta value which is dependent on said depth of interaction and said incident angle of said gamma ray.

8. The method of claim 6, wherein the step (ii) of generating a y delta value includes the steps of:
   (i) measuring said incident angle of said gamma ray along said axial field of view of said scintillator;
   (ii) determining a depth of interaction of said gamma ray in said scintillator; and
   (iii) generating said y delta value which is dependent on said depth of interaction and said incident angle of said gamma ray.

9. The method of claim 4, wherein said steps (a) and (b) are performed while said detectors are configured in the coincidence detection mode.

10. A method of improving resolution of an image in a gamma camera imaging system, the imaging system including a first crystal and a second crystal, the method comprising the steps of:
    (a) registering a first coordinate value of a first scintillation event generated by a first gamma ray interacting with said first crystal;
    (b) determining an incident angle of said first gamma ray;
    (c) generating a first correction value to correct in-crystal plane displacement of said first coordinate value, wherein said first correction value is a function of said determined incident angle of said first gamma ray; and
    (d) determining an entry point of said first gamma ray into said first crystal based on said first coordinate value and said first correction value.

11. The method of claim 10 further comprising the steps of:
    (e) registering a second coordinate value of a second scintillation event generated by a second gamma ray interacting with said second crystal, said second gamma ray emitted in coincidence with said first gamma ray along a line of response;
    (f) generating a second correction value to correct in-crystal plane displacement of said second coordinate value, wherein said second correction value is a function of an incident angle of said second gamma ray, an energy value of said second gamma ray, and multiple parameters of said second crystal; and
    (g) determining an approximate entry point of said second gamma ray into said second crystal based on said second coordinate value and said second correction value.

12. The method of claim 11, wherein said step (f) of generating a second correction value further comprises the steps of:
    (i) determining said incident angle of said second gamma ray;
    (ii) determining a distance along a line of response of said second gamma ray between a front surface of said second crystal and a back surface of said second crystal;
    (iii) determining a depth of interaction of said second scintillation event within said second crystal; and
    (iv) computing said second correction value based on said depth of interaction of said second scintillation event and a cotangent of said incident angle of said second gamma ray.

13. The method of claim 10, wherein said step (c) of generating a first correction value further comprises the steps of:
    (i) determining a distance along a line of response of said first gamma ray between a front surface of said first crystal and a back surface of said first crystal;
    (ii) determining a depth of interaction of said first scintillation event within said first crystal; and
    (iii) computing said first correction value based on said depth of interaction and a cotangent of said incident angle of said first gamma ray.

14. A gamma camera system comprising:
    a plurality of scintillation detectors each capable of detecting a plurality of photons and recording position coordinate values associated with said photons; and
    a data processing system coupled to each of said detectors, wherein said data processing system is configured to provide a correction value for a position coordinate value of one of said photons, wherein said correction value represents a positional displacement of said coordinate value, wherein said correction value is a function of an incident angle and an energy value of said photon, multiple parameters of said scintillation detectors, and a distance between two of said scintillation detectors.

15. The gamma camera system of claim 14, wherein the plurality of scintillation detectors are configurable to operate in either a coincidence mode or a single-photon mode, and wherein said data processing system is configured to provide said correction value when said scintillation detectors are configured to operate in said coincidence mode.

16. The gaamma camera system of claim 14, wherein each of said scintillation detectors comprises a scintillator, and wherein said multiple parameters comprise a thickness of each of said scintillators and a field of view of each of said scintillation detectors.

17. A gamma camera system comprising:
    a pair of detectors for detecting gamma rays, each of said detectors including one of a pair of scintillators, each of the detectors for detecting and generating coordinate values in response to scintillation interactions induced in said scintillators by said gamma rays; and a processor coupled to receive each of said coordinate values from each of said detectors, wherein said processor is configured to correct a positional displacement of one of said interactions by generating a correction value for said interaction and modifying a coordinate value for said interaction based on said correction value, wherein said correction value is computed as a function of a distance between said scintillators.

18. The gamma camera system of claim 17, wherein said correction value is further computed as a function of a thickness of each of said scintilators, an attenuation coefficient of each of said scintillators, and fields of view of each of said scintillators.

19. The gamma camera system of claim 17, wherein the scintillators are crystalline scintillators, and wherein the positional displacement is an in-crystal plane displacement.

20. The gamma camera system of claim 17, wherein the pair of detectors are configurable to detect gamma rays in either a coincidence mode or a single-photon mode.

21. A gamma camera system comprising:

a pair of detectors for detecting gamma rays, each of said detectors including at least one of a plurality of scintillation crystals, each of the detectors for detecting and generating coordinate values in response to scintillation interactions in said scintillation crystals; and a processor coupled to receive each of said coordinate values from each of said detectors, wherein said processor is configured to correct in-crystal plane displacement of the coordinate values by determining correction values for said coordinate values and adjusting said coordinate values based on corresponding correction values, wherein each of said correction values is a function of an incident angle of at least one of said gamma rays and a distance between said scintillation crystals.

22. The gamma camera system of claim 21, wherein said detectors are uncollimated.

23. The gamma camera system of claim 21, wherein said detectors are configurable to operate in either a coincidence mode or a single-photon mode, and wherein said processor is configured to correct said in-crystal plane displacement when said pair of detectors are configured to operate in said coincidence mode.

24. The gamma camera system of claim 21, wherein each said correction value further is a function of an energy value of one of said gamma rays and a plurality of parameters of said scintillation crystals.

25. The gamma camera system of claim 24, wherein said plurality of parameters of said scintillation crystals includes a thickness of each of said scintillation crystals, an attenuation coefficient of each of said scintillation crystals, a density of each of said scintillation crystals, and axial and transaxial fields of view of each of said scintillation crystals.

* * * * *